(12) United States Patent
Hall

(10) Patent No.: US 7,998,417 B2
(45) Date of Patent: Aug. 16, 2011

(54) PARTICULATE MATTER SENSOR WITH A HEATER

(75) Inventor: Matthew Hall, Austin, TX (US)

(73) Assignee: Board of Regents, University of Texas System, Austin, TX (US)

( * ) Notice: Subject to any disclaimer, the term of this patent is extended or adjusted under 35 U.S.C. 154(b) by 296 days.

(21) Appl. No.: 12/196,478

(22) Filed: Aug. 22, 2008

(65) Prior Publication Data

US 2010/0044246 A1 Feb. 25, 2010

(51) Int. Cl.
| | |
|---|---|
| G01N 27/00 | (2006.01) |
| G01N 31/12 | (2006.01) |
| G01N 7/00 | (2006.01) |
| G01N 21/00 | (2006.01) |
| G01N 31/00 | (2006.01) |
| G01N 33/00 | (2006.01) |
| G01N 37/00 | (2006.01) |

(52) U.S. Cl. ............. 422/98; 422/83; 422/94; 73/23.31; 73/28.01

(58) Field of Classification Search .......................... None
See application file for complete search history.

(56) References Cited

U.S. PATENT DOCUMENTS

| | | | |
|---|---|---|---|
| 2,307,602 A | 1/1943 | Penney | |
| 3,826,574 A | 7/1974 | Brown, Jr. | |
| 4,121,458 A | 10/1978 | Fort | |
| 4,656,832 A | 4/1987 | Hukihisa et al. | |
| 4,713,964 A | 12/1987 | Ioannides | |
| 4,939,466 A | 7/1990 | Johnson et al. | |
| 5,008,628 A | 4/1991 | Kirgmont et al. | |
| 5,104,513 A | 4/1992 | Lee et al. | |
| 5,264,272 A | 11/1993 | Tanabe et al. | |
| 5,290,606 A | 3/1994 | Hestevik et al. | |
| 5,302,935 A | 4/1994 | Chatterjee | |
| 5,608,155 A | 3/1997 | Ye et al. | |
| 5,795,454 A | 8/1998 | Friese et al. | |
| 5,892,140 A | 4/1999 | Wood | |
| 5,922,946 A | 7/1999 | Hirota et al. | |
| 5,942,190 A | 8/1999 | Kato et al. | |
| 5,948,963 A * | 9/1999 | Kato et al. | ...................... 73/23.2 |
| 6,076,393 A | 6/2000 | Kato et al. | |

(Continued)

FOREIGN PATENT DOCUMENTS

DE 4236711 5/1993

(Continued)

OTHER PUBLICATIONS

Young, Lee W., "International Search Report", (Aug. 15, 2008),1-3.

(Continued)

Primary Examiner — Jill Warden
Assistant Examiner — Charles Hammond
(74) Attorney, Agent, or Firm — Jeffrey T. Holman

(57) ABSTRACT

An apparatus to detect particulate matter. The apparatus includes a sensor electrode, a shroud, and a heater. The electrode measures a chemical composition within an exhaust stream. The shroud surrounds at least a portion of the sensor electrode, exclusive of a distal end of the sensor electrode exposed to the exhaust stream. The shroud defines an air gap between the sensor electrode and the shroud and an opening toward the distal end of the sensor electrode. The heater is mounted relative to the sensor electrode. The heater burns off particulate matter in the air gap between the sensor electrode and the shroud.

36 Claims, 12 Drawing Sheets

U.S. PATENT DOCUMENTS

| | | | |
|---|---|---|---|
| 6,161,421 | A | 12/2000 | Fang et al. |
| 6,202,469 | B1* | 3/2001 | Nakamura et al. ............ 73/23.31 |
| 6,214,208 | B1 | 4/2001 | Ando et al. |
| 6,327,891 | B1* | 12/2001 | Noda et al. .................... 73/31.05 |
| 6,557,393 | B1 | 5/2003 | Gokhfeld et al. |
| 6,634,210 | B1 | 10/2003 | Bosch et al. |
| 6,705,152 | B2 | 3/2004 | Routkevitch et al. |
| 6,763,699 | B1 | 7/2004 | Hunter et al. |
| 6,971,258 | B2 | 12/2005 | Rhodes et al. |
| 7,041,153 | B2 | 5/2006 | Totoki et al. |
| 7,063,731 | B2 | 6/2006 | Roe |
| 7,406,855 | B2 | 8/2008 | Tikkanen et al. |
| 2003/0014966 | A1 | 1/2003 | Hirota et al. |
| 2003/0061862 | A1* | 4/2003 | Kondo et al. ................. 73/23.31 |
| 2003/0116435 | A1* | 6/2003 | Satou et al. ................... 204/424 |
| 2003/0121251 | A1 | 7/2003 | Kelley et al. |
| 2004/0014234 | A1* | 1/2004 | Uchihara et al. ................ 422/80 |
| 2005/0178675 | A1 | 8/2005 | Hall |
| 2006/0016246 | A1 | 1/2006 | Rhodes et al. |
| 2006/0174690 | A1* | 8/2006 | Nishio et al. ................... 73/23.2 |
| 2007/0089399 | A1 | 4/2007 | Rhodes et al. |
| 2007/0261471 | A1* | 11/2007 | Kondo et al. ................... 73/23.2 |
| 2007/0271903 | A1 | 11/2007 | Rhodes et al. |
| 2008/0265870 | A1 | 10/2008 | Nair et al. |
| 2009/0056416 | A1 | 3/2009 | Nair et al. |
| 2009/0113983 | A1* | 5/2009 | Krafthefer .................... 73/23.31 |

FOREIGN PATENT DOCUMENTS

| | | |
|---|---|---|
| DE | 19536705 | 3/1997 |
| DE | 19817402 | 9/1999 |
| JP | 60-123757 | 7/1985 |
| JP | 64-20441 | 1/1989 |

OTHER PUBLICATIONS

Young, Lee W., "Written Opinion of the International Searching Authority", (Aug. 15, 2008),1-10.

Young, Lee W., "International Search Report", (Nov. 25, 2008),1-2.

Young, Lee W., "Written Opinion of the International Searching Authority", (Nov. 25, 2008),1-6.

Hauser, "Method for Measuring Particles in Gas Flow e.g. vehicle exhaust", DE19536705, (Apr. 3, 1997),Abstract.

Hauser, "Sensor Device for Quantitative Evaluation of Particles Suspended in Gas Flow, e.g. smoke particles in diesel engine exhaust gas", DE19817402, (Sep. 30, 1999),Abstract.

Moosmueller, et al., "Time Resolved Characterization of Diesel Particulate Emissions", *Environmental Science and Technology*, vol. 35, No. 4, (2001),781-787.

Olsen, Kaj K., "International Search Report", (Feb. 13, 2004), 1-5.

McCall, Eric S., "Office-Action for U.S. Appl. No. 11/039,365 sent Feb. 2, 2009", 1-6.

Hauser, "English Translation of DE-19536705", (Apr. 3, 1997),1-8.

Hauser, "English Translation of DE-19817402", (Sep. 30, 1999),1-6.

* cited by examiner

PARTICULATE MATTER SENSOR WITH A HEATER

FEDERALLY SPONSORED RESEARCH OR DEVELOPMENT

The U.S. Government has certain rights in this invention as provided for by the terms of Grant No. DE-FC26-06NT42966 awarded by the U.S. Department of Energy.

BACKGROUND

Internal combustion engines (e.g. diesel engines) typically generate an exhaust flow that contains varying amounts of particulate matter (PM). The amount and size distribution of particulate matter in the exhaust flow tends to vary with engine operating conditions, such as fuel injection timing, injection volume, injection pressure, or the engine speed to load relationship. Adjustment of these conditions may be useful in reducing particulate matter emissions and average particle size in the particulate matter from the engine. Reducing particulate matter emissions from internal combustion engines is environmentally favorable. In addition, particulate matter measurements for diesel exhaust is useful for on-board (e.g., mounted on a vehicle) diagnostics of PM filters and reduction of emissions through combustion control.

Conventional technologies that may be used for on-board monitoring of particulate matter in exhaust flow include wire sensor applications. Wire sensors apply a high voltage between two electrodes and measure the current or charge between the electrodes. The electrode measurement is correlated with a specific particulate matter concentration. However, wire electrode sensors are subject to the de-calibration and baseline drift of the sensor due to accumulation of soot (i.e., particulate matter deposit) on and between the electrodes.

A conventional solution to remove the particulate matter deposit from the electrodes implements a wire coil heater near the concentration of particulate matter deposits. The wire coil heater is wound around the electrodes to heat the electrodes and thermally break down the accumulated deposit. With the heater and electrode exposed to a relatively high concentration of particulate matter in the exhaust stream, the heater consumes high amounts of energy to burn off the particulate matter and prevent sensor signal corruption.

SUMMARY

Embodiments of an apparatus are described. In one embodiment, the apparatus includes a sensor electrode, a shroud, and a heater. The sensor electrode measures a chemical composition within an exhaust stream. The shroud surrounds at least a portion of the sensor electrode, exclusive of a distal end of the sensor electrode exposed to the exhaust stream. The shroud defines an air gap between the sensor electrode and the shroud and an opening toward the distal end of the sensor electrode. The heater is mounted relative to the sensor electrode. The heater burns off particulate matter in the air gap between the sensor electrode and the shroud. Other embodiments of the apparatus are also described.

Embodiments of a system are also described. In one embodiment, the system includes a sensor, a heater, and a processor. The sensor detects a chemical composition within an exhaust stream. The sensor includes a sensor electrode and a shroud surrounding the sensor electrode. The shroud defines an air gap between the sensor electrode and the shroud. The air gap is exposed to the exhaust stream. The heater is mounted relative to the sensor electrode. The heater burns off particulate matter in the air gap between the sensor electrode and the shroud. The processor receives a sensor signal from the sensor electrode and controls the heater. Other embodiments of the system are also described.

Embodiments of a method are also described. In one embodiment, the method is a method for burning off a particulate matter from a sensor in an exhaust stream. The method includes detecting a chemical composition within the exhaust stream using a sensor which includes a sensor electrode and a shroud surrounding the sensor electrode to define an air gap between the sensor electrode and the shroud. The air gap is exposed to the exhaust stream. The method also includes activating a heater in response to a trigger condition. The heater is mounted relative to the sensor electrode. The method also includes heating the particulate matter in the air gap to burn off the particulate matter in the air gap between the sensor electrode and the shroud. Other embodiments of the method are also described.

Embodiments of another method are also described. In one embodiment, the method is a method for making a particulate matter concentration sensor. The method includes mounting a sensor electrode partially within a shroud, forming an air gap between the sensor electrode and the shroud. The method also includes mounting the sensor electrode and the shroud at least partially within a sensor housing. The distal ends of the shroud and the sensor electrode extend beyond a threshold of the sensor housing. The method also includes mounting a heater approximately adjacent to a portion of the shroud. The heater burns off particulate matter in the air gap between the sensor electrode and the shroud. Other embodiments of the method are also described.

Other aspects and advantages of embodiments of the present invention will become apparent from the following detailed description, taken in conjunction with the accompanying drawings, illustrated by way of example of the principles of the invention.

DETAILED DESCRIPTION

Figure 1:
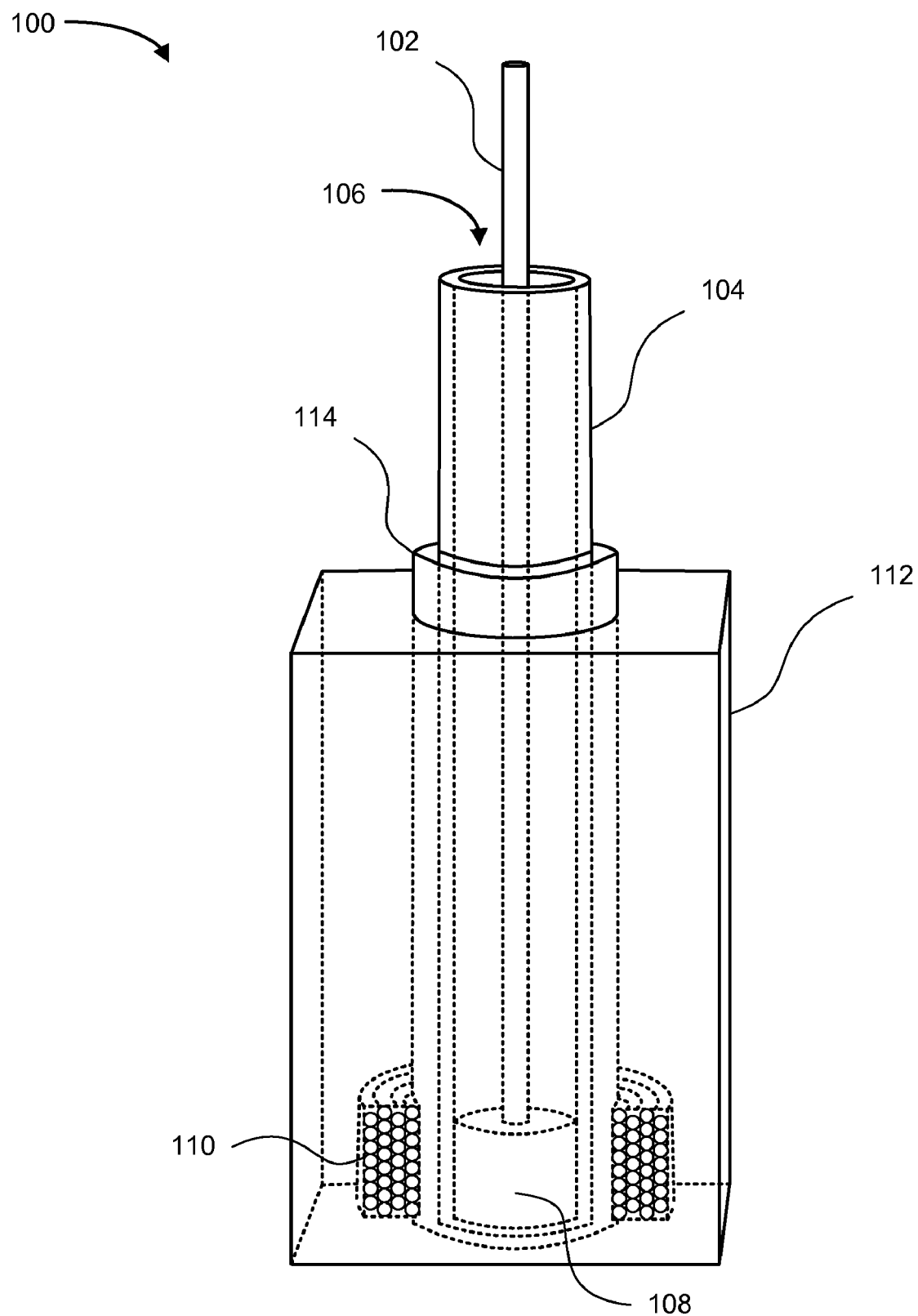
FIG. 1 depicts a schematic diagram of one embodiment of an electrode assembly.

FIG. 1 depicts a schematic diagram of one embodiment of an electrode assembly 100. The illustrated electrode assembly 100 includes a wire electrode 102. In some embodiments, the wire electrode 102 may be made of NiChrome wire. In other embodiments, the wire electrode 102 may be made of other materials with characteristics for high heat tolerance and/or low oxidation.

The electrode assembly 100 also includes a shroud 104. The illustrated shroud 104 may be metallic or some other conductive material. In some embodiments, the shroud 104 is biased to function as an electrical reference point or ground relative to the wire electrode 102. This facilitates measurement of ambient conditions in the vicinity of the wire electrode 102. The shroud 104 at least partially defines an air gap 106 surrounding the wire electrode 102. In some embodiments, the air gap 106 may be defined as the radial distance from the outer surface of the wire electrode 102 to the inner surface of the shroud 104. In some embodiments, the shroud 104 is at a radial distance from the wire electrode 102 to prevent electrical arcing between the shroud 104 and the wire electrode 102. Electrical arcing may occur when particulate matter builds up within the air gap.

In the illustrated electrode assembly 100, the wire electrode 102 and the shroud 104 have constant radii along their respective lengths. As a result, the air gap 106 also has a constant width. In some embodiments, the wire electrode 102 and the shroud 104 may have radii that vary with respect to length. For example, some embodiments may incorporate a wider radius at the distal end of the shroud 104 to create a larger air gap 106 at that point, to allow more particulate material to deposit on the shroud 104 or wire electrode 102 before electrically discharging between the wire electrode 102 and the shroud 104.

The electrode assembly 100 of FIG. 1 also includes an electrode attachment point 108. The electrode attachment point 108 is located at the proximal end of the shroud 104, opposite the distal end of the wire electrode 102. The electrode attachment point 108 serves to mount the wire electrode 102 to the electrode assembly 100. The electrode attachment point 108 is made of material that is able to mechanically support the wire electrode 102. In some embodiments, the electrode attachment point 108 is a non-electrically conductive support piece though which the conducting wire electrode 102 passes. Alternatively, the electrode attachment point 108 is an electrically conductive support piece, which provides support for both the wire electrode 102 and an electrically conductive path leading to the corresponding detection electronics.

The electrode assembly 100 also includes a heater 110. The heater 110 includes one or more devices for generating heat. In general, the heater 110 generates sufficient heat to exceed the thermal breakdown threshold of the particulate matter deposits that accumulate on the shroud 106 and/or the wire electrode 102. In some embodiments, the heater 110 includes one or more resistance heaters. An example of a resistance heater is a coil of resistive wire which generates heat in the wire coil when supplied with a current. In another embodiment, the heater 110 includes one or more inductance heaters. An example of an inductive heater is a wire coil that creates heat in the sensor electrode 102 when an electrical current is applied to the wire coil. In another embodiment, the heater 110 includes one or more combustion heaters. An example of a combustion heater is a flame jet.

In some embodiments, the location of the heater relative to the depth of the air gap (i.e. approximately from the distal open end of the shroud 104 to the electrode attachment point 108) can affect the amount of heat produced and electrical energy consumed in order to burn off deposited particulate matter. In some embodiments, the air gap 106 serves to remove the location of the heater 110 from areas of high particulate matter concentrations near the distal end of the wire sensor electrode 102 because the distal open end of the shroud 104 is exposed to the exhaust stream and is exposed to higher amounts of particulate matter. Lower amounts of particulate matter result in less energy and/or less frequent periods of activation to burn off particulate matter deposits.

In some embodiments, the air gap 106 is approximately between 1 and 3 centimeters deep from the distal end of the shroud 104 to the electrode attachment point 108. In other embodiments, the air gap is greater than 2 centimeters deep from the distal end of the shroud 104 to the electrode attachment point 108.

In some embodiments, the heater 110 is connected to an insulating shroud 114. The insulating shroud 114 which surrounds the shroud 104. The insulating shroud 114 serves as an insulating barrier between the conducting shroud 104 and the heater 110. In some embodiments, the insulating shroud 114 is made of a ceramic material. In other embodiments, the insulating shroud 114 is made of another insulating material. For embodiments in which the shroud 104 is not conductive, the additional insulating shroud 114 may be omitted.

The insulating shroud 114 also may serve as an electrically insulating barrier between the shroud 104 and a sensor housing 112. As illustrated, the sensor housing 112 has a rectangular geometry. In other embodiments, the sensor housing 112 may have a cylindrical or other geometry to facilitate installation into a sensing environment.

In some embodiments, the heater 110 is mounted near the proximal end of the air gap 106. One advantage of mounting the heater 110 at the proximal end of the air gap 106 is apparent in the behavior of ceramic material when heated. When heated, ceramics can become electrically conductive. To reduce the chance of electrical discharge of the wire electrode 102 against the heat-induced electrically conductive ceramic around the heater 110, the heater 110 is mounted at the proximal end of the air gap 106 to reduce concentrations of particulate matter at the location of the heater 110.

Figure 2:
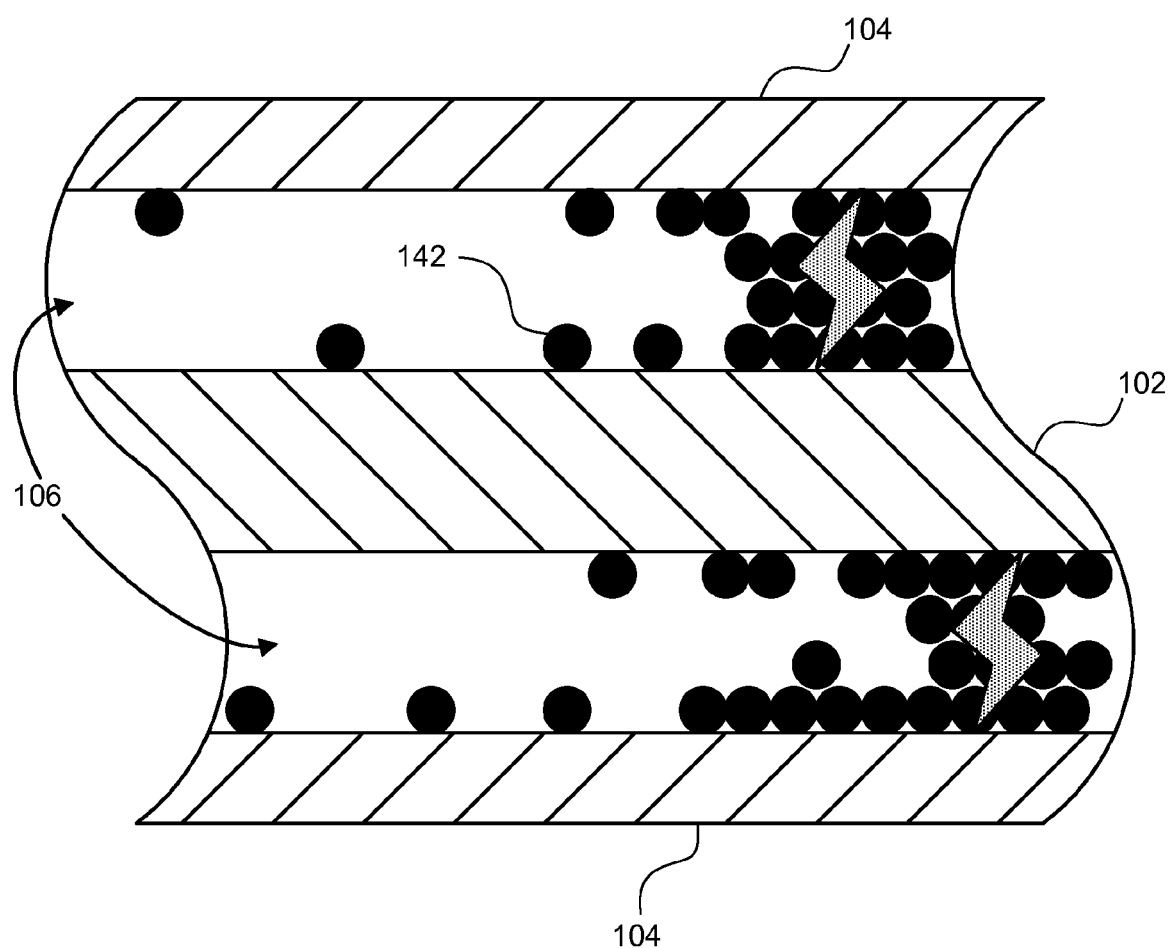
FIG. 2 depicts a cross-sectional view of an electrode assembly channel with particulate matter deposits.

FIG. 2 depicts a cross-sectional view of an electrode assembly air gap 106 with particulate matter deposits 142. In the illustrated embodiment, the particulate matter deposits 142 are deposited in the air gap 106. In particular, the particulate matter 142 collects between the wire electrode 102 and the conductive shroud 104, creating an electrically conductive path or short between the shroud 104 and the sensor electrode 102. In other words, the particulate matter 142 forms an electrical connection which alters the resulting sensor signal and/or destroys the functionality of the electrode assembly 100.

The particulate matter 142 has a thermal breakdown threshold. If the threshold is exceeded, the particulate matter 142 burns off and is drawn out of the air gap 106 by a passing exhaust stream so that the particulate matter 142 does not form an electrically conductive path between the shroud 104 and the sensor electrode 102. Isolating the conductive shroud 104 from the wire electrode 102 preserves the fidelity of the sensor signal generated by the electrode assembly 100.

Figure 3A:
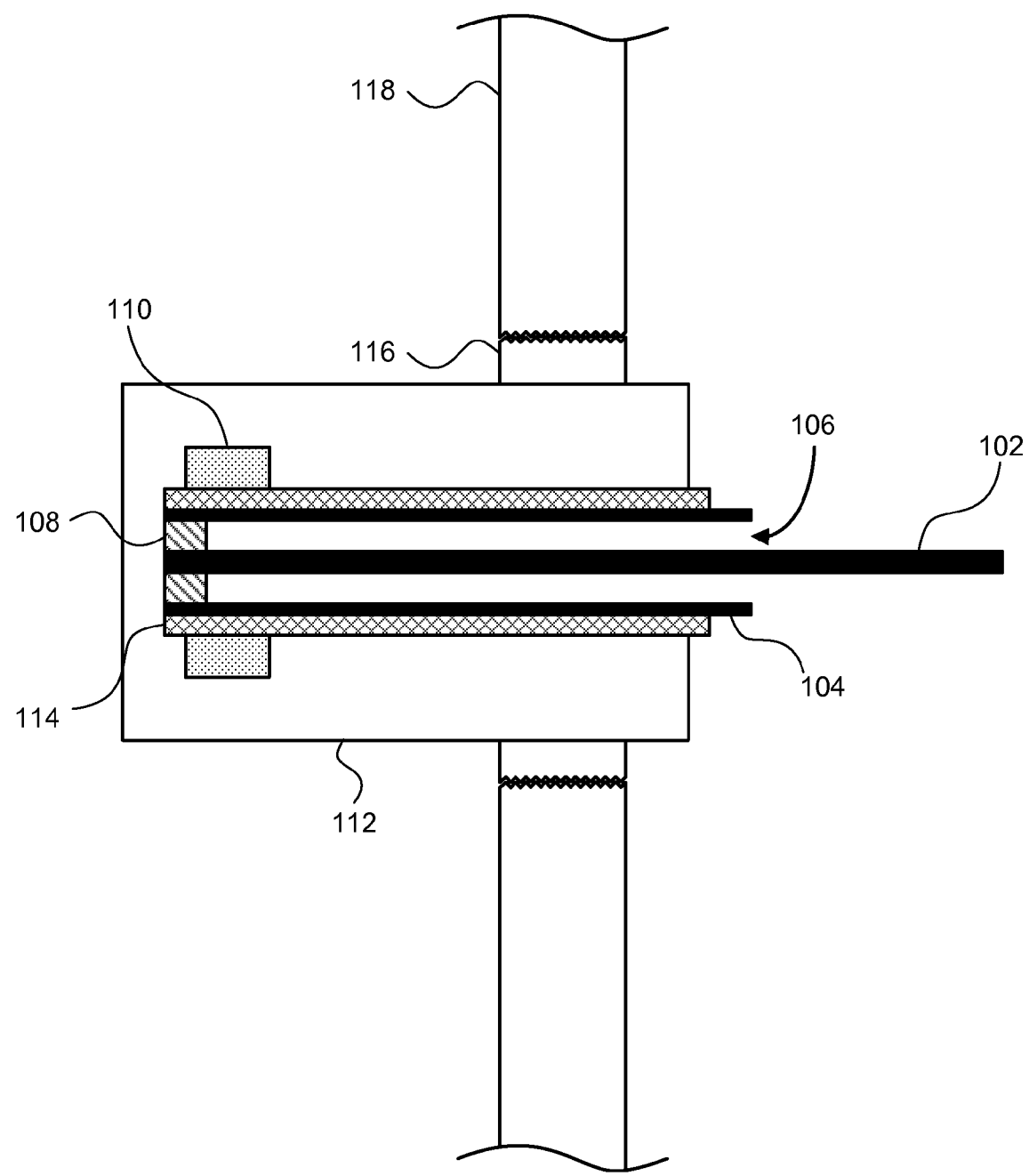
FIG. 3A depicts a cross-sectional view of another embodiment of the electrode assembly of FIG. 1.

FIG. 3A depicts a cross-sectional view of another embodiment of the electrode assembly of FIG. 1. Similar numbers depict similar components. In the illustrated embodiment, the wire electrode 102 is surrounded by a conductive shroud 104. The conductive shroud 104 is surrounded by an insulating shroud 114. The conductive shroud 104 partially defines an air gap 106 surrounding part of the length of the wire electrode 102.

The illustrated embodiment includes a heater 114 mounted on the outer surface of the insulating shroud 114. The wire electrode 102 is mounted in the electrode attachment point 108. FIG. 3A also illustrates a mounting surface 116. In the illustrated embodiment, the mounting surface 116 is a threaded surface made to match up with an exhaust wall 118 with matching threads. In some embodiments, the mounting surface 116 forms a seal that is substantially air tight when mounted in the exhaust wall 118. In some embodiments, the mounting surface 116 may be a gasket or some other mechanism for mounting the sensor assembly in the exhaust wall 118.

Figure 3B:
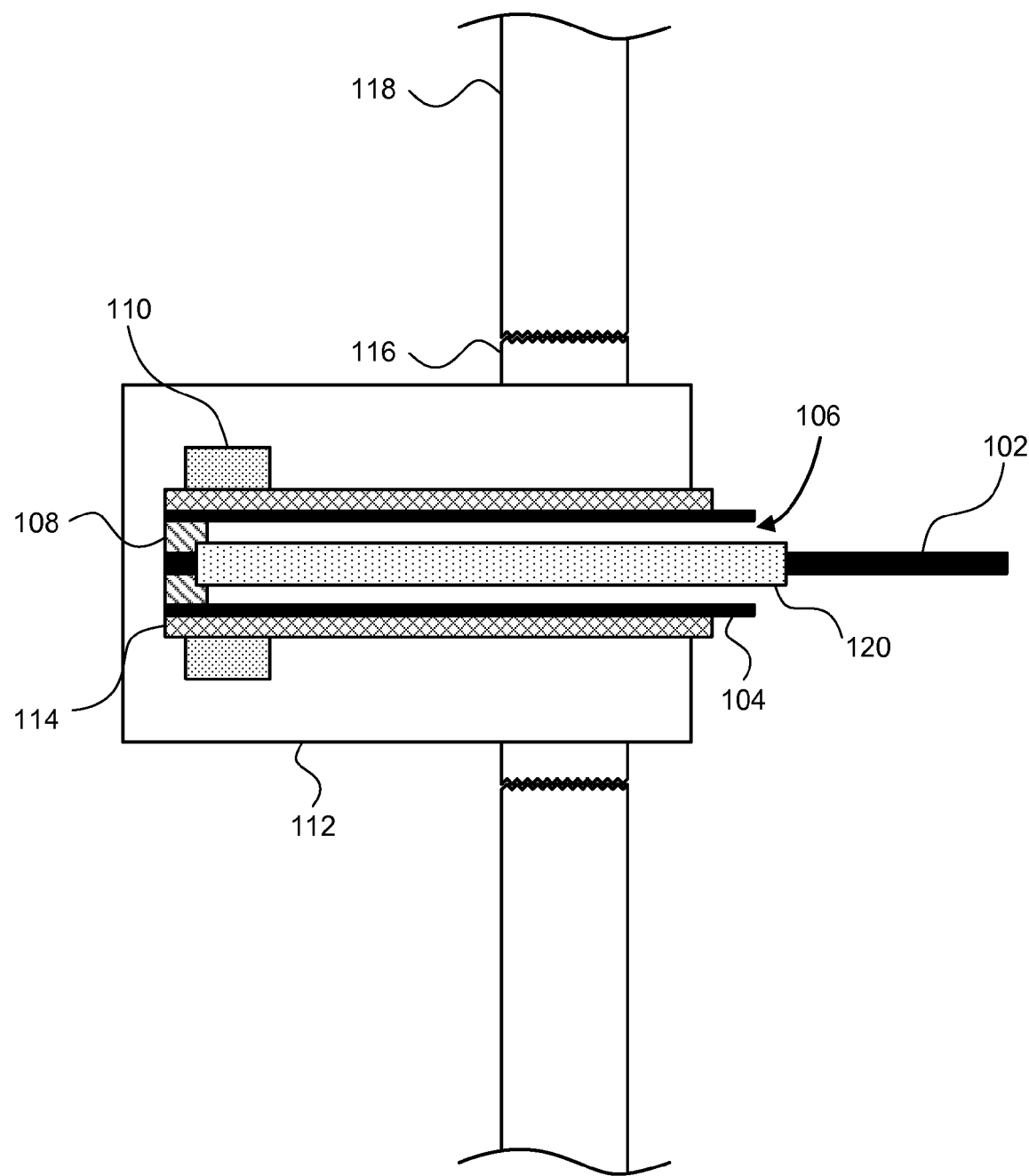
FIG. 3B depicts a cross-sectional view of the electrode assembly of FIG. 3A with an electrode coating.

FIG. 3B depicts a cross-sectional view of one embodiment of an electrode assembly of FIG. 1 with an electrode coating 120. The electrode coating 120 further prevents or resists the accumulation of particulate matter on the wire electrode 102 and/or the conductive shroud 104. In some embodiments, the electrode coating 120 is a catalytic material on the surface of the sensor electrode 102. The catalytic coating 120 facilitates surface reactions with the particulate matter on the sensor electrode 102 to remove the particulate matter from the surface of the sensor electrode 102. In other embodiments, the electrode coating 120 is a non-catalytic coating to resist adhesion of particulate matter to the sensor electrode 102. Some examples of catalytic coatings include precious metals such as platinum, palladium, and rhodium, although other precious metals may be used. Examples of non-catalytic coatings include metal oxides (e.g., aluminum oxide) and metals which are non-catalytic under typical conditions, (e.g., chrome or nickel). Other types of catalytic and non-catalytic coatings may be used. In some embodiments, the electrode coating 120 may cover more than about half of the length of the wire electrode 102. In some embodiments, the electrode coating 120 may cover more than about 80% of the length of the wire electrode 102. In other embodiments, the electrode coating 120 covers substantially all of the length of the wire electrode 102. In other embodiments which implement a non-conductive coating, the electrode coating 120 may cover less than half of the wire electrode 102 to help keep a base portion of the wire electrode 102 free of contaminants. Other embodiments may implement an electrode coating 120 to cover a different amount, depending on the length of the wire electrode 102 relative to the surrounding conductive shroud 104. In some embodiments, the conductive shroud 104 may parallel more than about half of the length of the wire electrode 102. Other embodiments may use different shroud lengths and geometries, depending on the position and sensitivity of the wire electrode 102.

Figure 4A:
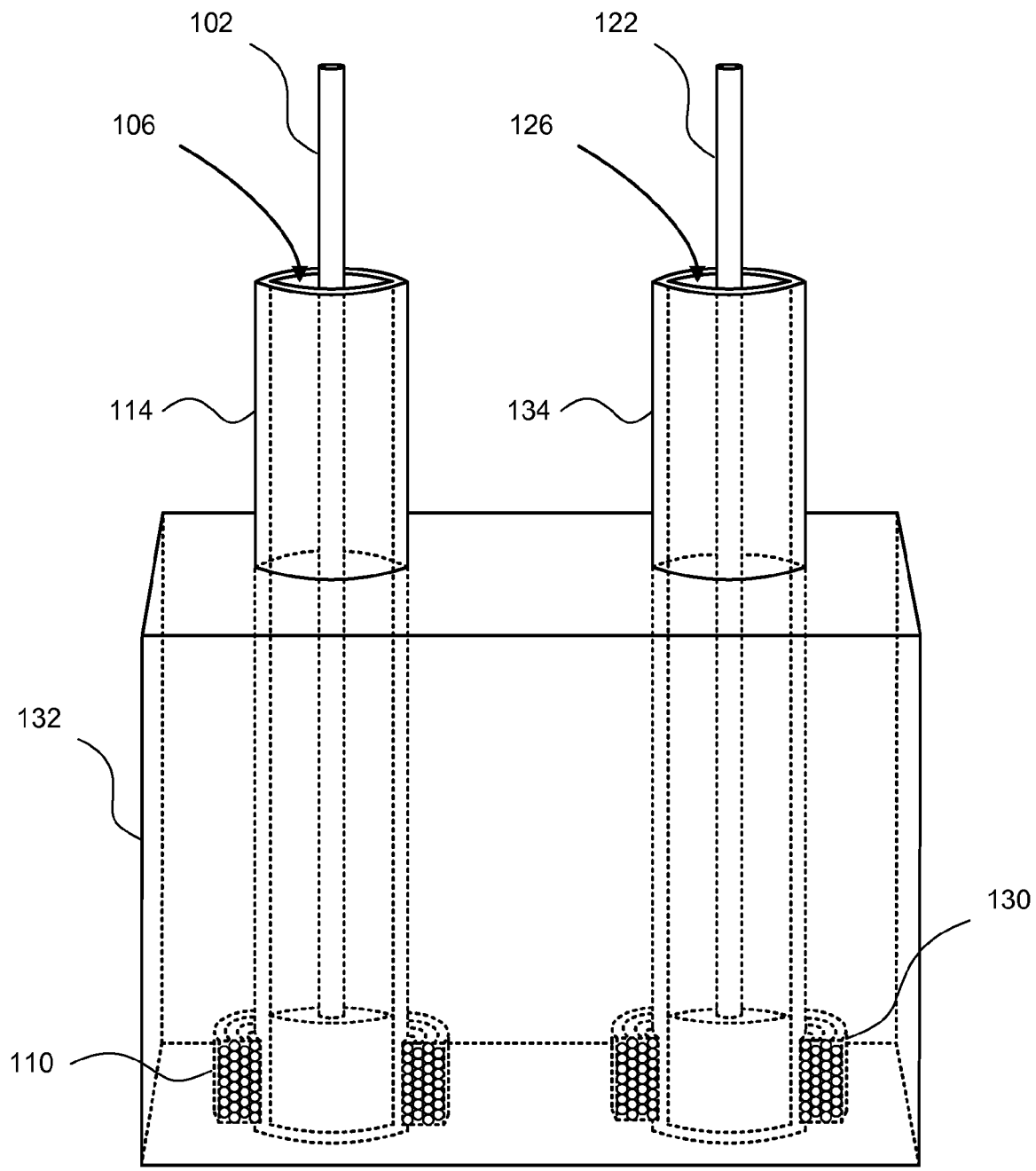
FIG. 4A depicts a schematic diagram of one embodiment of a dual electrode assembly.

FIG. 4A depicts a schematic diagram of one embodiment of a dual electrode assembly. In some embodiments, the electrode assembly of the first wire electrode 102 and the electrode assembly of the second wire electrode 122 are mounted in a simple sensor housing 132. In other embodiments, the sensor housing 132 is divided into two separate housings to house each electrode assembly in separate housings. In some embodiments, the sensor housing 132 may have electrical shielding between the first and second wire electrodes 102 and 122 to reduce signal distortion.

In some embodiments, the first heater 110 and the second heater 130 are combined into a single heater. In other embodiments, the heaters 110 and 130 are separate and electrically shielded to substantially prevent or reduce risk of "burn out" in the heater coils. In some embodiments, the electrode assembly of the first electrode 102 and the electrode assembly of the second electrode 122 are substantially identical.

Figure 4B:
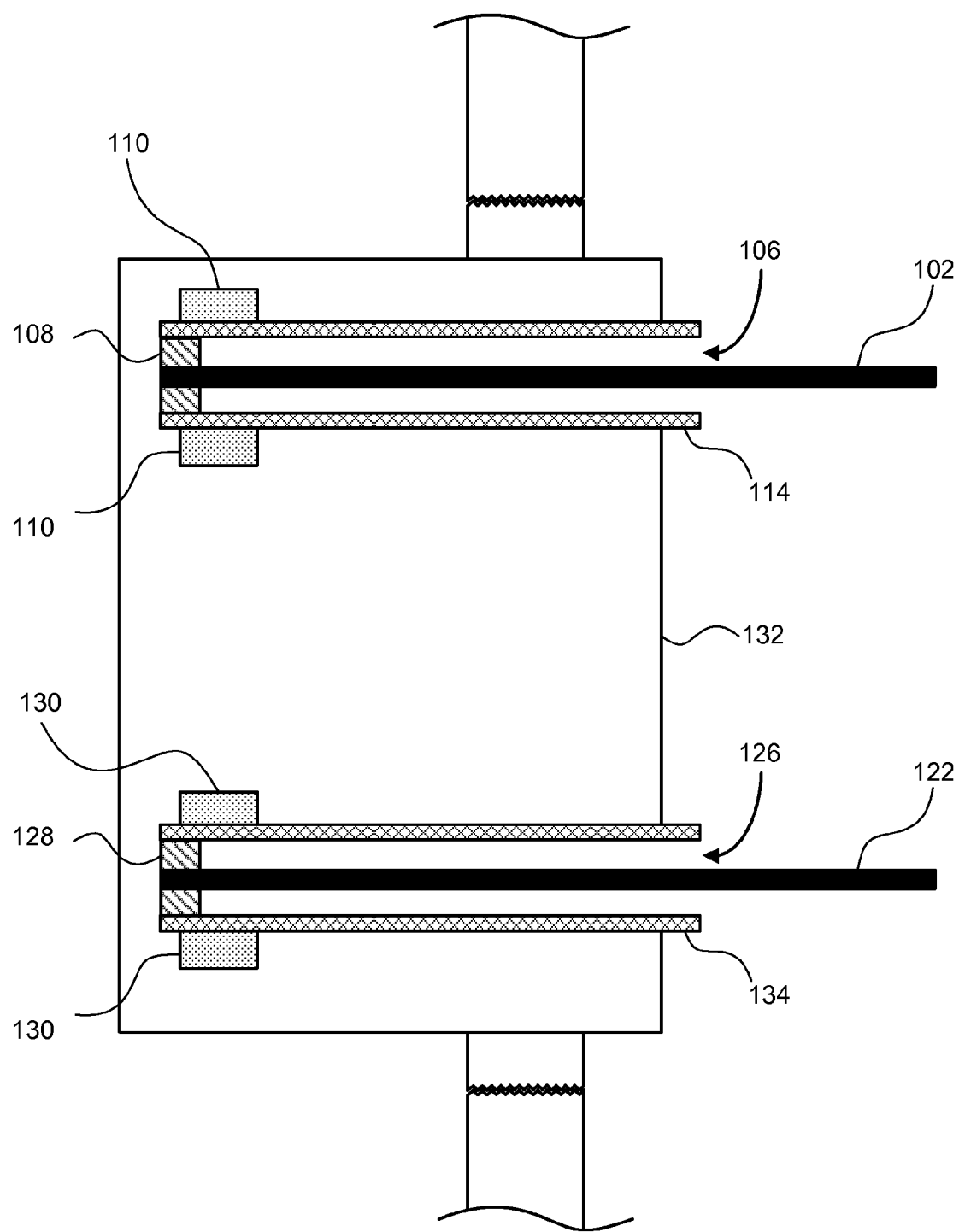
FIG. 4B depicts a cross-sectional view of another embodiment of a dual electrode assembly.

FIG. 4B depicts a cross-sectional view of another embodiment of a dual electrode assembly. In the illustrated embodiment, two sensor assemblies of FIG. 1 are mounted in one sensor housing 132. The measurement of electrical potential difference between the first wire electrode 102 a second wire electrode 122 facilitates particulate matter detection in a specimen. Operating voltages may be AC or DC and positive or negative relative to ground. In one embodiment, an operating range of the bias voltage is from about 500 V to about 2000 V, although other embodiments may use other specific voltages or a broad voltage range. The first and second wire electrodes 102 and 122 are mounted at a distance to avoid electrical discharge between the electrodes 102 and 122. The first wire electrode 102 is mounted to the electrode attachment point 108. The insulating shroud 114 partially defines an air gap 106 which partially surrounds the wire electrode 102.

The heater 110 is located on the proximal end of the sensor assembly. The heater 110 is located at the proximal end of the wire electrode 102 to reduce the amount of particulate matter to deposit in the region of the insulating shroud 114 where the heater is mounted. The location of the heater 110 requires a reduced amount of energy to burn off particulate matter deposits. The location of the heater 110 at the proximal end of the air gap 106 also reduces the frequency of activation periods of the heater 110 to maintain an acceptable level of particulate matter deposit. In some embodiments, the insulating shroud 114 may be ceramic.

In some embodiments, the assembly of FIG. 4B of the first electrode 102 is oriented downstream from the assembly of the second electrode 122 within the exhaust stream. In other embodiment, the assembly of the first electrode 102 is located side-by-side with the assembly of the second electrode 122 so that a line drawn from one electrode to the other would be approximately perpendicular to the flow of exhaust past the electrodes 102 and 122.

Figure 5:
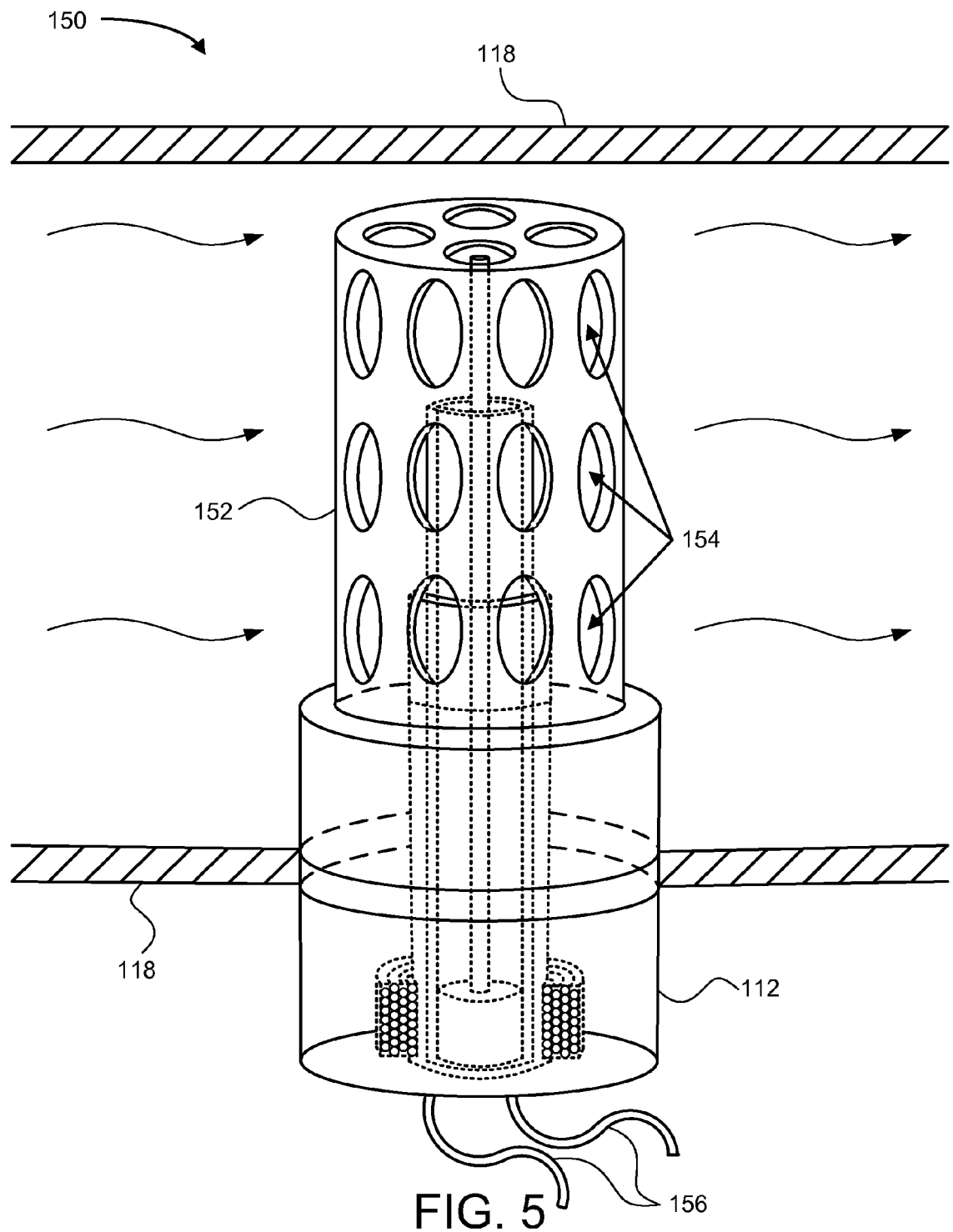
FIG. 5 depicts a schematic diagram of one embodiment of a particulate matter sensor with a protective electrode housing.

FIG. 5 depicts a schematic diagram of one embodiment of a particulate matter sensor 150 with a protective housing 152. In the illustrated embodiment, the protective housing 152 is mounted to the sensor housing 112. In some embodiments, the protective housing 152 and the sensor housing 112 are a unitary structure. In other embodiments, the protective housing 152 and the sensor housing 112 are formed separately, and the protective housing 152 is mounted to the sensor housing 112. In some embodiments, the protective housing 152 includes flow apertures 154 to allow exhaust to pass over the sensor electrode 102. In some embodiments, the flow apertures 154 are circular. In other embodiments, the flow apertures 154 are non-circular. In some embodiments, the protective housing 152 is a wire cage configured to mechanically protect the sensor electrode 102. In some embodiments, the protective housing 152 is made of metal. In other embodiments, the protective housing is made of a rigid, non-metallic material capable of withstanding the heat of the exhaust stream.

The sensor assembly 150 includes electrical leads 156 attached to one or more electrode attachment points 108. The electrical leads 156 may supply power to the sensor assembly 150. In other embodiments, the electrical leads 156 relay sensor signals from the wire electrode 102. Some embodiments may include more or less than two electrical leads 156.

Figure 6:
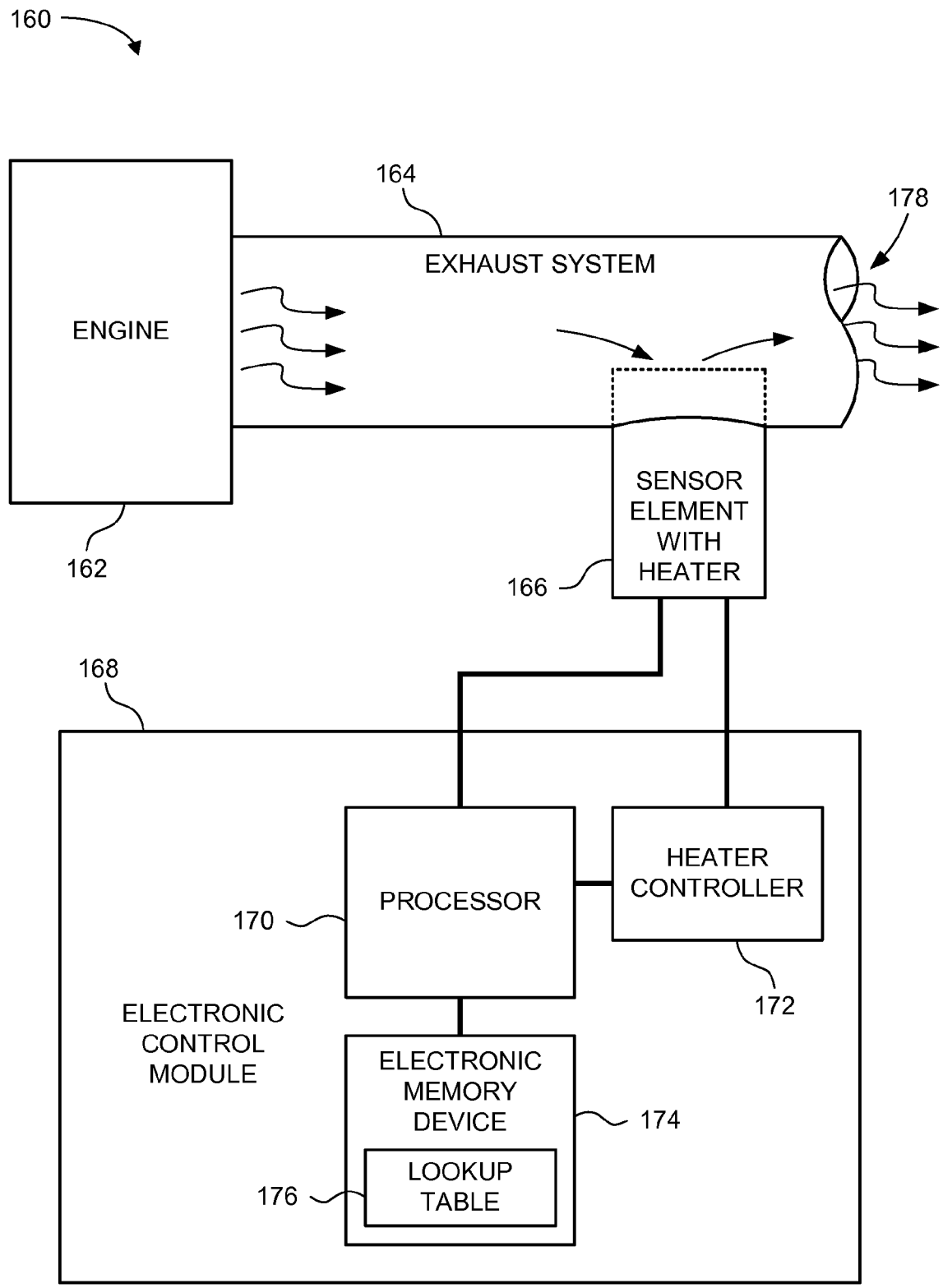
FIG. 6 depicts a block diagram of one embodiment of a particulate matter detection system.

FIG. 6 depicts a block diagram of one embodiment of a particulate matter detection system 160. The illustrated embodiment includes an engine 162. The engine 162 produces exhaust which moves along an exhaust system 164. The sensor 166 is inserted into the exhaust system 164 to detect particulate matter in the exhaust stream. The exhaust system 164 facilitates flow of the exhaust gases to an exhaust outlet 178. As the exhaust in the exhaust system 164 passes over the sensor 166, the sensor 166 detects the particulate matter within the exhaust by measuring changes in the electrical potential at the sensor 166.

The particulate matter detection system 160 also includes an electronic control module 168. The sensor 166 relays the sensor signal to the processor 170 of the electronic control module 168. In some embodiments, the processor 170 sends a signal to the heater controller 172 to activate the heater on the sensor 166 according to a timing scheme or on some other non-continuous basis. In some embodiments, the processor analyzes the signal from the sensor 166. If the signal is corrupted, the processor sends a signal to the heater controller 172. The heater controller 172 activates the heater on the sensor 166 and the heater of the sensor 166 burns off particulate matter deposits that corrupt the signal from the sensor 166. If the signal is not corrupt, the processor 170 sends the signal to the electronic memory device 174 of the electronic control module 168. The electronic memory device 174 compares the signal with data stored in a lookup table 176 to decipher the qualities of the exhaust in the exhaust system 164. The electronic memory device 174 may decipher a count of particulate matter particles within the exhaust. The electronic memory device 174 may compare the signal with data from the lookup table 176 to decipher particulate matter particle size in the exhaust. In some embodiments, the electronic memory device 174 deciphers one or more of the qualities of the exhaust in the exhaust system 164.

Some embodiments of the particulate measurement system 160 also may include one or more emissions control elements to emit neutralizing chemicals into the exhaust system 164 either before or after the sensor 166. It should also be noted that embodiments of the sensor 166 may be tolerant of fluctuations of certain gaseous constituents in an exhaust gas environment. In this way, the sensor 166 may be calibrated to measure particular chemicals or materials within an exhaust stream.

Figure 7:
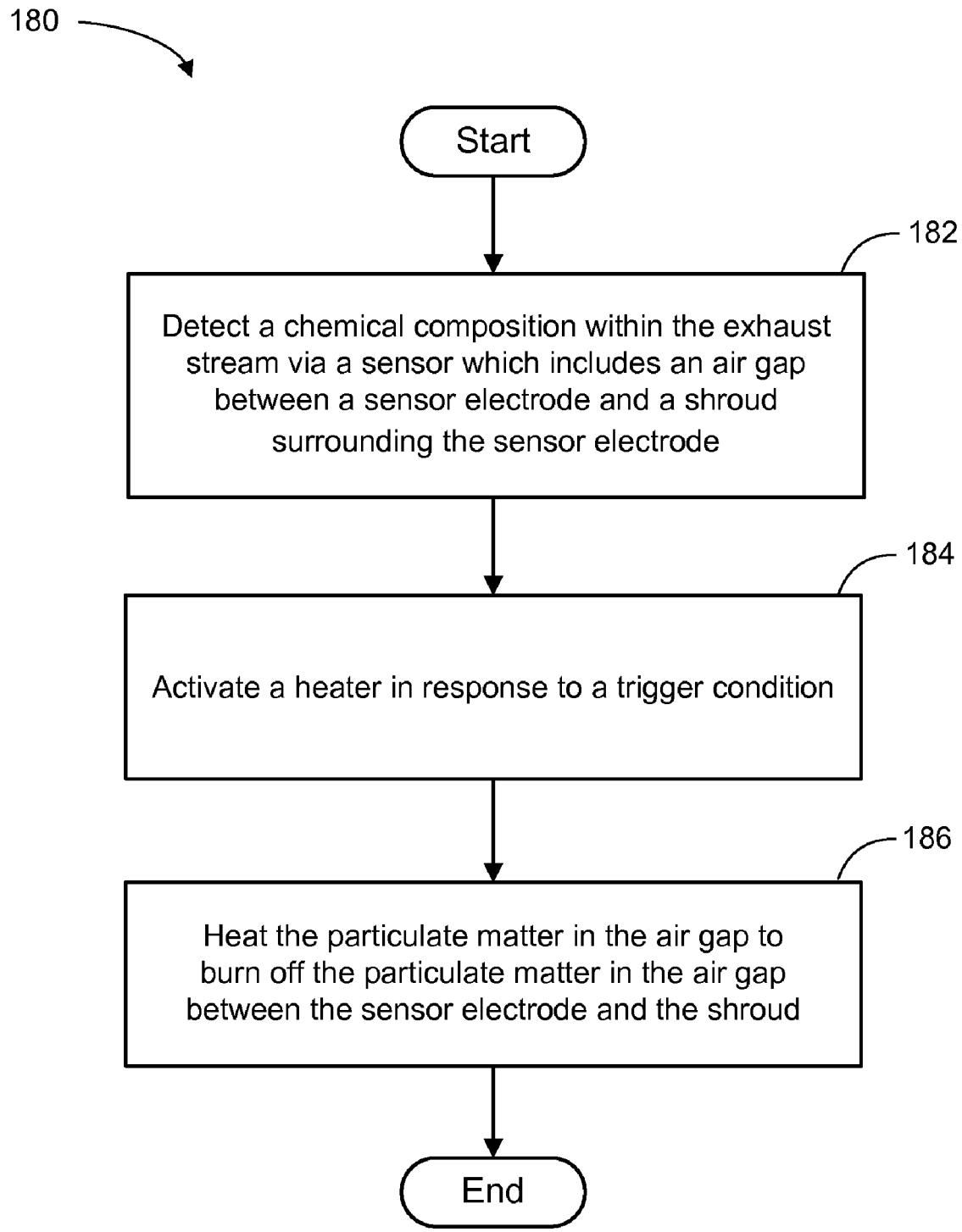
FIG. 7 depicts a block diagram of one embodiment of a method for operating a particulate matter sensor.

FIG. 7 depicts a schematic flowchart diagram of one embodiment of a method 180 for operating a particulate matter sensor. While certain particulate matter sensors and particulate matter sensor assemblies may be referenced in connection with the description of the method 180, embodiments of the method 180 may be implemented with other types of particulate matter sensors and particulate matter sensor assemblies. Additionally, embodiments of the method 180 may be implemented with various types of particulate matter measurement systems.

In the illustrated embodiment, a sensor 100 detects 182 a chemical composition within an exhaust stream. The sensor includes an air gap 106 between a sensor electrode 102 and a shroud 104. The shroud 104 surrounds the sensor electrode 102 and the air gap 106 is exposed to the exhaust stream.

In the illustrated embodiment, an electronic control module 168 activates 184 a heater 110 in response to a trigger condition. The heater 110 is mounted relative to the sensor electrode 102. The illustrated embodiment also includes a heater 110 to heat 186 the particulate matter in the air gap 106 between the sensor electrode 102 and the shroud 104.

Figure 8:
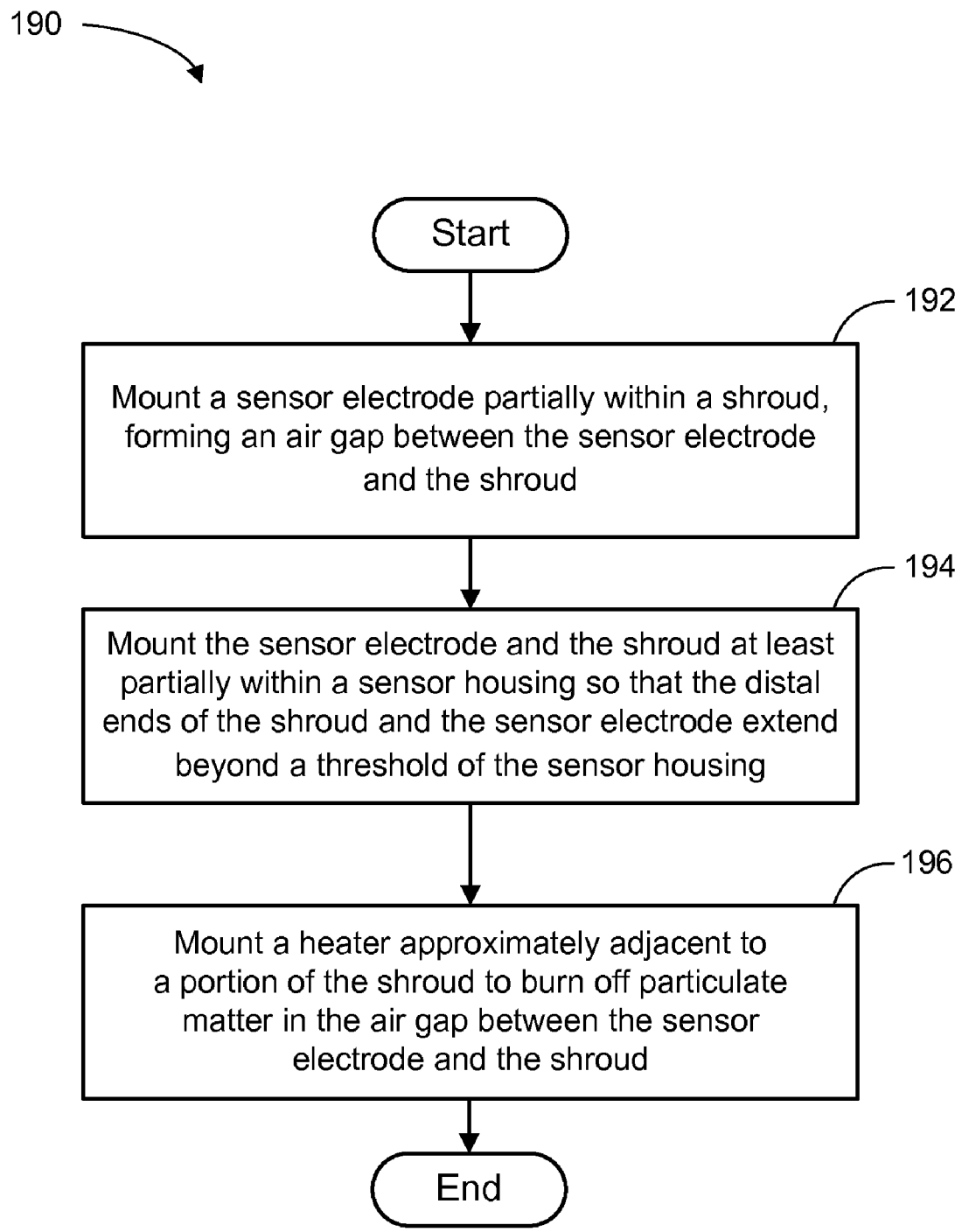
FIG. 8 depicts a block diagram of one embodiment of a method for making a particulate matter sensor.

FIG. 8 depicts a block diagram of one embodiment of a method 190 for making a particulate matter sensor. The illustrated method includes mounting 192 a sensor electrode 102 partially within a shroud 104 to form an air gap 106 between the sensor electrode 102 and the shroud 104. The method also includes mounting 194 the sensor electrode 102 and the shroud 104 at least partially within a sensor housing 112. The distal ends of the shroud 104 and the sensor electrode 102 extend beyond a threshold of the sensor housing 112. The method 190 also includes mounting 196 a heater 110 approximately adjacent to a portion of the shroud 104. The heater 110 burns off particulate matter in the air gap 104 between the sensor electrode 102 and the shroud 104.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Figure 9:
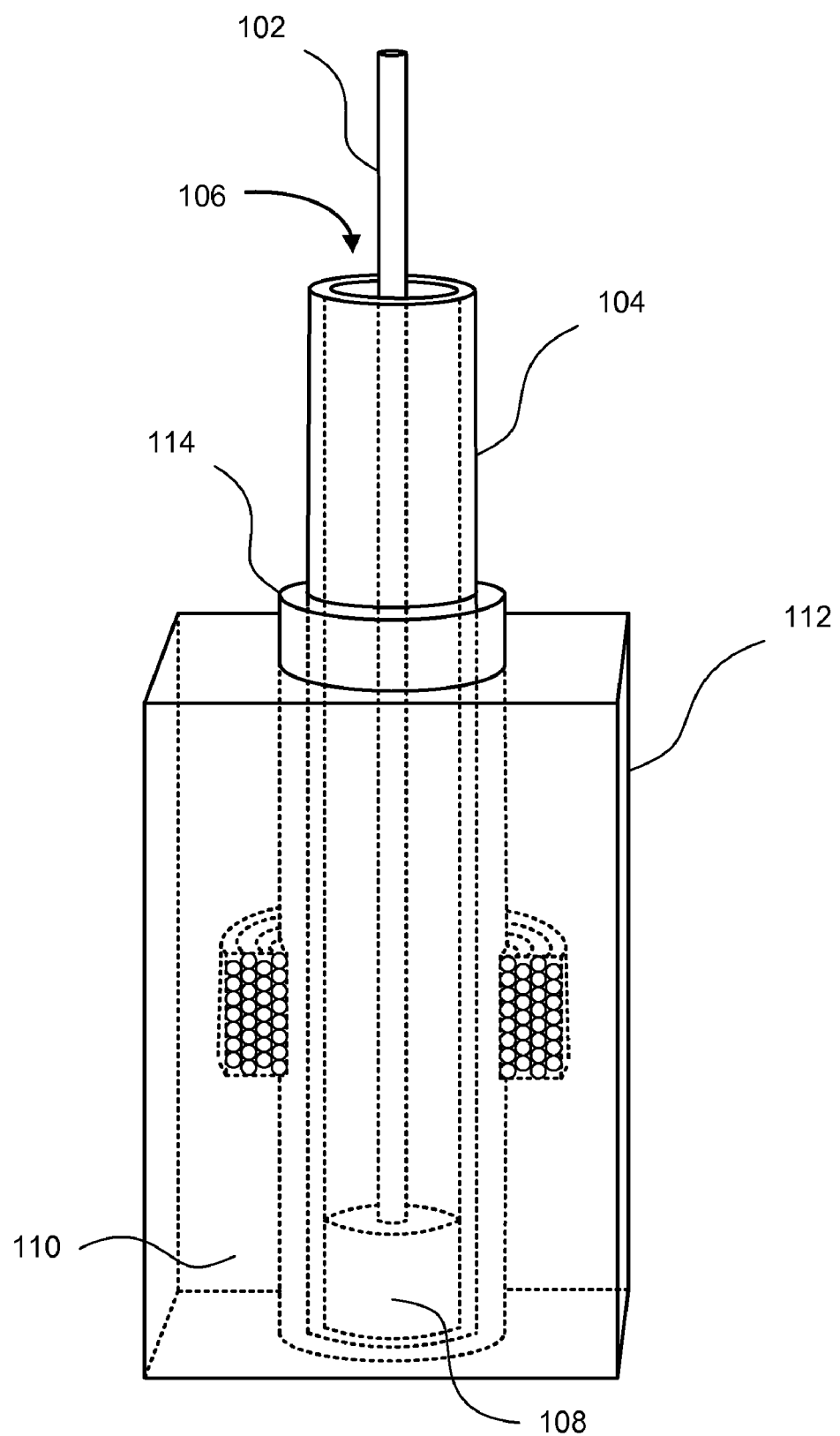
FIG. 9 depicts a schematic diagram of another embodiment of the sensor assembly of FIG. 1.

FIG. 9 depicts a schematic diagram of another embodiment of the sensor assembly 100 of FIG. 1. In the illustrated embodiment, the heater element 110 is located within the sensor housing 112 and at a distance from the electrode attachment point 108. In some embodiments, the heater 110 may be located closer or farther from the proximal end of the shroud 104 or the electrode attachment point 108.

Figure 10:
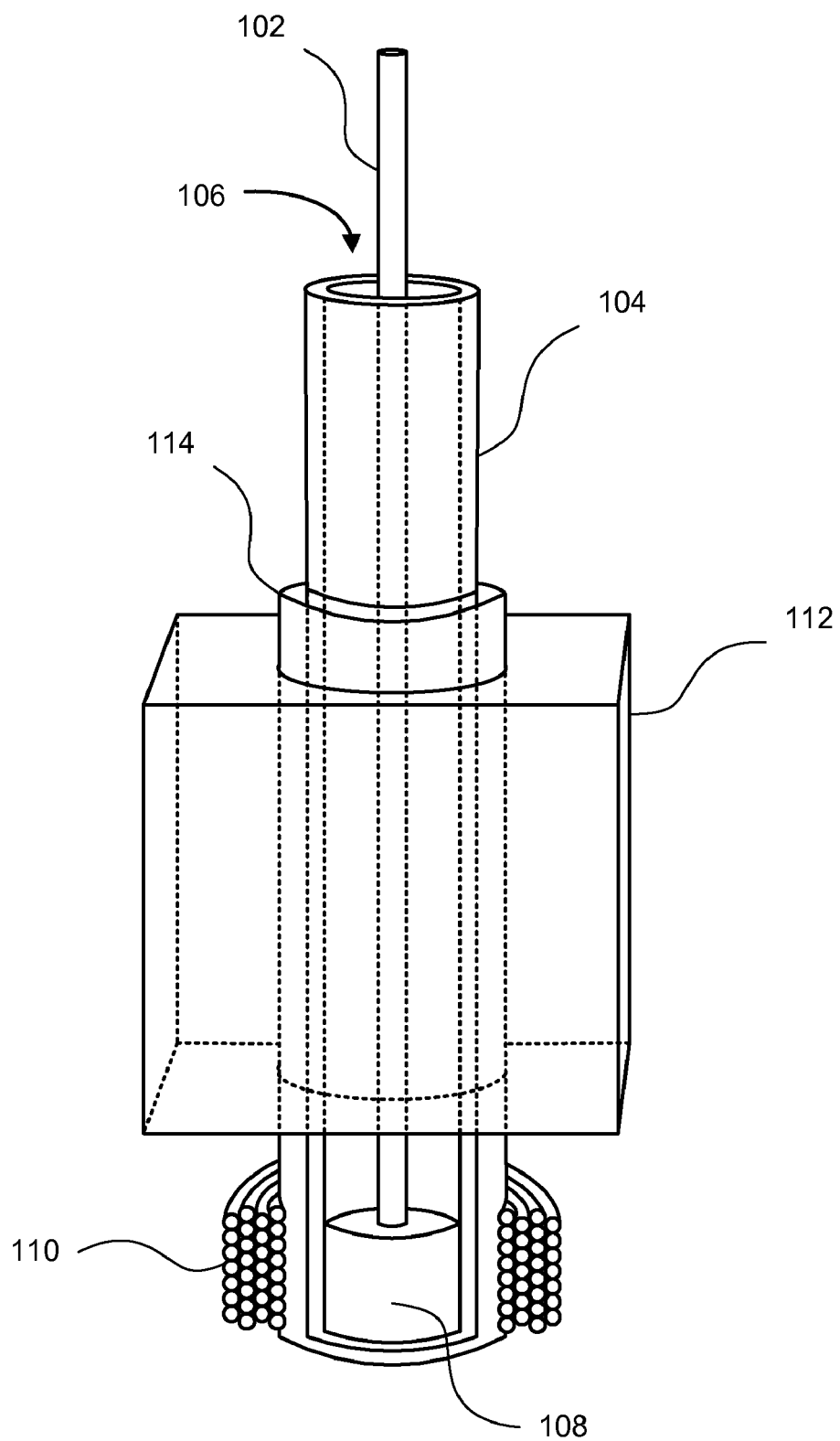
FIG. 10 depicts a schematic diagram of another embodiment of the sensor assembly of FIG. 1.

FIG. 10 depicts a schematic diagram of another embodiment of the sensor assembly 100 of FIG. 1. In the illustrated embodiment, the heater element 110 is located outside of the sensor housing 112. In some embodiments, the heater 110 may be located closer or farther from the proximal end of the shroud 104 or the electrode attachment point 108.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A sensor apparatus comprising:
   a sensor electrode to measure a chemical composition within an exhaust stream;
   a shroud to surround at least a portion of the sensor electrode, exclusive of a distal end of the sensor electrode exposed to the exhaust stream, wherein the shroud is configured to define an air gap between the sensor electrode and the shroud, and the shroud further defines an opening near the distal end of the sensor electrode, wherein the shroud is electrically conductive;
   an electrical lead coupled to the electrically conductive shroud to apply a bias voltage to the electrically conductive shroud; and
   a heater mounted relative to the sensor electrode, the heater to burn off particulate matter in the air gap between the sensor electrode and the shroud.

2. The sensor apparatus of claim 1, wherein the sensor electrode comprises a metallic wire.

3. The sensor apparatus of claim 1, further comprising a non-catalytic coating on a surface of the sensor electrode, the non-catalytic coating to resist adhesion of the particulate matter to the sensor electrode.

4. The sensor apparatus of claim 3, wherein the non-catalytic coating comprises a metal oxide.

5. The sensor apparatus of claim 1, further comprising a catalytic coating on a surface of the sensor electrode, the catalytic coating to facilitate surface reactions with the particulate matter for removal of the particulate matter from the surface of the sensor electrode.

6. The sensor apparatus of claim 5, wherein the catalytic coating comprises a precious metal.

7. The sensor apparatus of claim 1, wherein the bias voltage is greater than about 500 V.

8. The sensor apparatus of claim 7, wherein the bias voltage is approximately between 500-2000 V.

9. The sensor apparatus of claim 1, further comprising an electrically insulating shroud mounted to approximately encircle the electrically conductive shroud.

10. The sensor apparatus of claim 1, wherein the shroud is located at a radial distance within a range of about 1-2 mm from the surface of the electrode.

11. The sensor apparatus of claim 1, wherein the heater comprises a resistance heater.

12. The sensor apparatus of claim 11, wherein the resistance heater comprises a coil of electrically resistive wire.

13. The sensor apparatus of claim 1, wherein the heater comprises an inductance heater.

14. The sensor apparatus of claim 1, wherein the heater comprises a combustion heater.

15. The sensor apparatus of claim 1, wherein the heater is located inside the shroud.

16. The sensor apparatus of claim 1, wherein the heater is located outside the shroud.

17. The sensor apparatus of claim 1, further comprising a sensor housing, wherein the heater is located inside the sensor housing.

18. The sensor apparatus of claim 1, further comprising a sensor housing, wherein the heater is located outside the sensor housing and outside the exhaust stream.

19. The sensor apparatus of claim 1, wherein the heater is configured to generate heat substantially continuously.

20. The sensor apparatus of claim 1, wherein the heater is configured to generate heat intermittently.

21. The sensor apparatus of claim 1, wherein the heater is located approximately at a distance of 0-25 mm from the distal end of the shroud.

22. The sensor apparatus of claim 21, wherein the heater is located at a distance of approximately 15 mm from the distal end of the shroud.

23. A system for detecting particulate matter, the system comprising:
a sensor to detect particulate matter within an exhaust stream, the sensor comprising a sensor electrode and a shroud surrounding the sensor electrode, wherein the shroud is exclusive of a distal end of the sensor electrode exposed to the exhaust stream, wherein the shroud is configured to define an air gap between the sensor electrode and the shroud, wherein the air gap is exposed to the exhaust stream through an opening defined by the shroud near the distal end of the sensor electrode, and wherein the shroud is electrically conductive;
a heater mounted relative to the sensor electrode, the heater to burn off particulate matter in the air gap between the sensor electrode and the shroud; and
a processor to receive a sensor signal from the sensor electrode and to control the heater, wherein the processor is further configured to apply a bias voltage to the electrically conductive shroud.

24. The system of claim 23, wherein the electrode is mounted at least partially inside a sensor housing.

25. The system of claim 23, further comprising a non-catalytic coating on a surface of the sensor electrode, the non-catalytic coating to resist adhesion of the particulate matter to the sensor electrode.

26. The sensor apparatus of claim 23, wherein the non-catalytic coating comprises a metal oxide.

27. The system of claim 23, further comprising a catalytic coating on a surface of the sensor electrode, the catalytic coating to facilitate surface reactions with the particulate matter for removal of the particulate matter from the surface of the sensor electrode.

28. The sensor apparatus of claim 27, wherein the catalytic coating comprises a precious metal.

29. The system of claim 23, wherein the processor is further configured to control a frequency of operation of the heater.

30. The system of claim 23, wherein the processor is further configured to control a temperature of operation of the heater.

31. The system of claim 23, further comprising an electrode housing to at least partially enclose the distal end of the sensor electrode, the electrode housing comprising apertures to allow the exhaust stream to flow across the sensor electrode.

32. The system of claim 23, further comprising:
a second sensor to detect the chemical composition within the exhaust stream;
a second shroud surrounding the second sensor electrode to define an air gap between the second sensor electrode and the second shroud, wherein the air gap is exposed to the exhaust stream; and
a second heater mounted relative to the second sensor electrode, the second heater to burn off particulate matter in the air gap between the second sensor electrode and the second shroud;
wherein the processor is further configured to receive a second sensor signal from the second sensor electrode and to control the second heater.

33. The system of claim 32, wherein the first and second electrodes are mounted to a single sensor housing.

34. The system of claim 23, further comprising an electrically insulating shroud mounted to approximately encircle the electrically conductive shroud.

35. The sensor apparatus of claim 1, wherein the electrical lead is further configured to apply the bias voltage to the electrically conductive shroud according to a processor.

36. The system of claim 23, further comprising an electrical lead coupled to the processor, wherein the electrical lead is configured to apply the bias voltage to the electrically conductive shroud according to the processor.

* * * * *